(12) United States Patent
Schmidt et al.

(10) Patent No.: US 7,205,539 B1
(45) Date of Patent: Apr. 17, 2007

(54) SAMPLE CHARGING CONTROL IN CHARGED-PARTICLE SYSTEMS

(75) Inventors: John Schmidt, Oakland, CA (US); David Crewe, Sunnyvale, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/077,519

(22) Filed: Mar. 10, 2005

(51) Int. Cl.
*G01N 23/00* (2006.01)

(52) U.S. Cl. .................................. 250/310; 250/307
(58) Field of Classification Search ................. 250/310
See application file for complete search history.

(56) References Cited

U.S. PATENT DOCUMENTS

| | | | |
|---|---|---|---|
| 6,465,781 B1 * | 10/2002 | Nishimura et al. ......... 250/306 |
| 6,765,205 B2 | 7/2004 | Ochiai et al. | |
| 2003/0141451 A1 * | 7/2003 | Sato et al. ................. 250/310 |
| 2005/0023486 A1 * | 2/2005 | Takakuwa et al. ....... 250/492.2 |

OTHER PUBLICATIONS

McCord, M.A. "Use of Ultraviolet Light in charged Particle Systems to Reduce Charging and Contamination", IBM Technical Disclosure Bulletin, Pub. No. 10a, Mar. 1990, pp. 157-158, Yorktown, U.S.A.

* cited by examiner

*Primary Examiner*—David Vanore
(74) *Attorney, Agent, or Firm*—Okamoto & Benedicto LLP

(57) ABSTRACT

One embodiment disclosed relates to a charged-particle beam apparatus configured with sample charging control. A stage is configured to hold a sample, and a column for generating a charged-particle beam and for directing the beam to an area of the sample. A light beam is generated by an irradiation source and is directed to the area. Bias circuitry is configured to apply a stage bias voltage such that an electric field is created with respect to the sample. Control circuitry is coupled to the irradiation source and to the bias circuitry. The control circuitry is configured to direct the light beam onto the area at a same time as the stage bias voltage is applied to the sample. Other embodiments are also disclosed.

33 Claims, 5 Drawing Sheets

100

United States Patent US 7,205,539 B1

SAMPLE CHARGING CONTROL IN CHARGED-PARTICLE SYSTEMS

BACKGROUND OF THE INVENTION

1. Field of the Invention

The present invention relates generally to charged-particle beam systems, such as those used for specimen inspection, review, parametric characterization and for other purposes.

2. Description of the Background Art

Charged-particle beam systems include, for example, electron beam imaging (EBI) systems, electron stimulated x-ray (ESX) systems, and other systems. These systems are often applied to inspect, review or measure insulating samples, such as, for example, a semiconductor wafer with an insulating layer. The insulating layer on a semiconductor wafer may be, for example, silicon dioxide, silicon nitride, or other insulating materials. When a charged-particle beam impinges upon such an insulating sample, charges may build up in the sample due to the negatively-charged electrons being deposited on or embedded within the insulating layer, or due to a net positive charge which remains when secondary and/or backscattered electrons leave the surface, or combinations of these effects.

This charging of the sample can be detrimental to the performance of the charged-particle imaging or measurement system. For example, the charge distribution can create a net electrostatic potential on the film surface that will change the landing energy of the primary electron beam. Such changes in electrostatic potential are difficult to model quantitatively as they depend upon the film stack's resistance and capacitance which may strongly vary with process layer deposition and etching parameters. Uncertainty in the actual landing energy may adversely impact the performance of the system. For example, inaccuracies may be introduced into an ESX system's determination of film thickness or composition since the ESX system utilizes landing energy to predict characteristic x-ray production from the materials under measurement.

One conventional approach for reducing the impact of charging is to expose the sample with a beam from an alternate charged-particle source, typically an electron "flood gun." This may be done to put the sample into a particular charge state, and to reduce or control the charging effects observed during subsequent measurements. However, this approach has various disadvantages and difficulties. For example, it may leave the sample in a charge state which depends on the history of the prior bombardment or treatment of the sample. Furthermore, the flood beam itself is subject to deflection and other effects discussed above. Finally, a flood gun is typically costly to add and difficult to locate in close proximity to or coincident with the primary charged-particle beam, or to operate simultaneous with the primary beam.

As discussed above, problems and difficulties are caused by charging of samples being examined in a charged-particle beam system. Hence, it is desirable to improve techniques for controlling sample charging in charged-particle beam systems.

SUMMARY

One embodiment of the invention pertains to a charged-particle beam apparatus configured with sample charging control. A stage is configured to hold a sample, and a column for generating a charged-particle beam and for directing the beam to an area of the sample. A light beam is generated by an irradiation source and is directed to the area. Bias circuitry is configured to apply a stage bias voltage such that an electric field is created with respect to the sample. Control circuitry is coupled to the irradiation source and to the bias circuitry. The control circuitry is configured to direct the light beam onto the area at a same time as the stage bias voltage is applied to the sample.

Another embodiment of the invention pertains to a method of sample charging control in a charged-particle beam system. A light beam is generated and irradiated onto an area of a sample held by a stage, and a stage bias voltage is applied such that an electric field is created with respect to the sample. The stage bias voltage is applied concurrently with the irradiation by the light beam.

Other embodiments are also disclosed.

DETAILED DESCRIPTION

Figure 1:
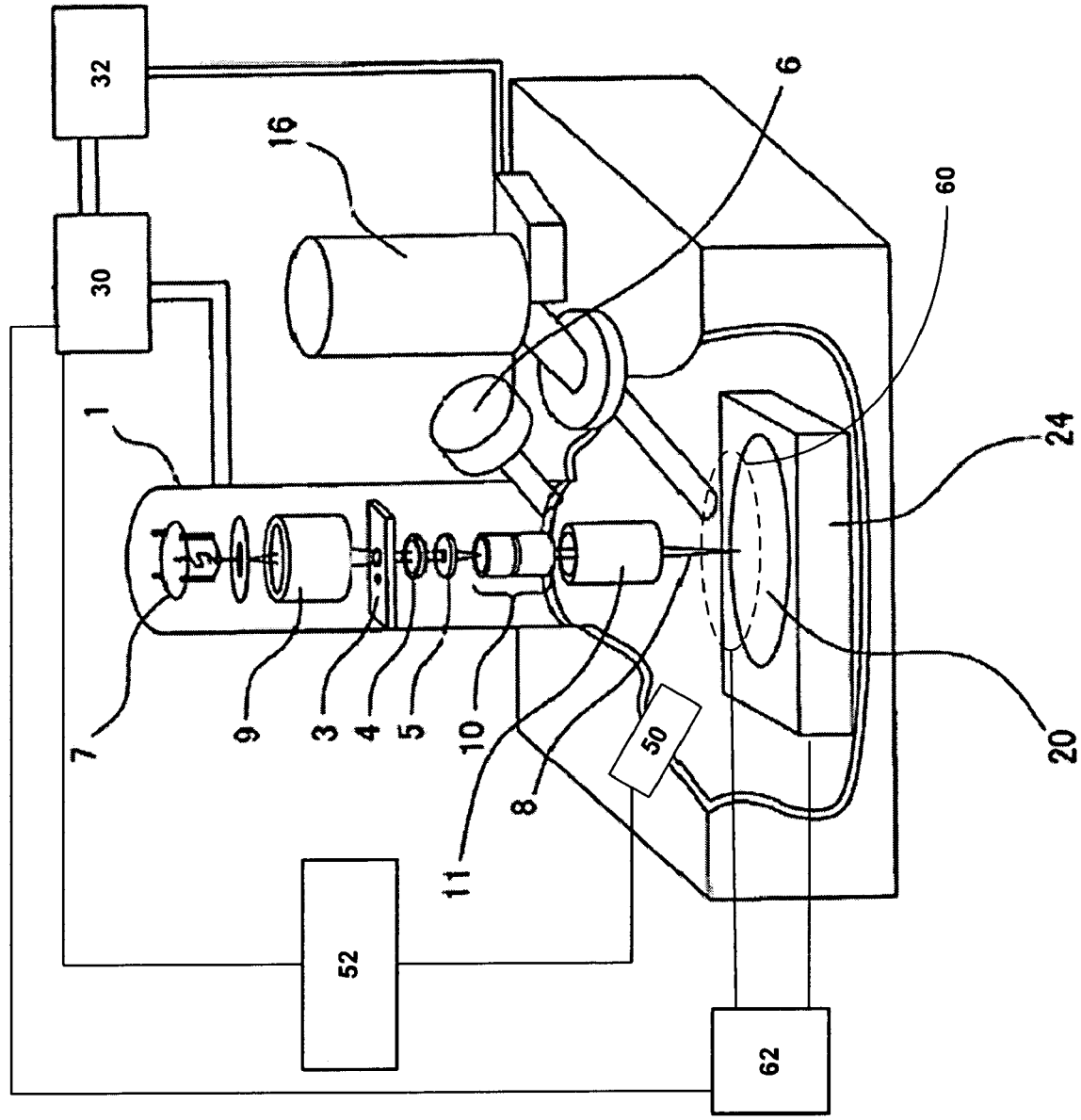
FIG. 1 is schematic diagram of an apparatus in accordance with an embodiment of the invention.

FIG. 1 is schematic diagram of an example apparatus 100 in accordance with an embodiment of the invention. The example apparatus 100 comprises an electron stimulated x-ray system. In other embodiments, the apparatus may comprise an electron beam imaging system, or other charged-particle beam systems.

The example apparatus 100 includes an electron beam optical system 1. The electron beam optical system 1 includes an electron gun or other source 7, an electron lens 9 for focusing the electron beam 8 emitted from the electron gun 7, an aperture 3 for cutting out unnecessary portions of the electron beam 8, a blanking coil 4, a Faraday cup 5, an electron beam scanning coil 10, and an objective lens 11. The Faraday cup 5 has a through-hole that normally allows the electron beam 8 to pass through. The blanking coil 4 may deflect the electron beam 8 to fall on the Faraday cup 5 when measuring current of the electron beam 8.

The example apparatus 100 in FIG. 1 also includes a secondary electron detector 6, a specimen stage 24, an x-ray detector 16, and a light or radiation source or flood gun 50, and a conductive grid 60. The secondary electron detector 6 may be configured to detect secondary electrons which have been emitted from the wafer 20 due to the irradiation of the electron beam 8 onto the wafer 20. The specimen stage 24, on which the wafer 20 is placed, is configured to be movable. The x-ray detector 16 may be configured to detect x-rays radiated from the wafer 20 due to the impingement of the electron beam 8 onto the wafer 20. The light or radiation source 50 may be configured to emit or project light of UV frequencies (or other frequencies) onto the wafer 20. The conductive grid 60 may be positioned above the specimen 20, wherein the electron beam 8 may pass through an opening in the grid 60 so as to impinge upon the specimen 20.

A main controller 30 may be configured to control and coordinate the various components of the apparatus 100. An x-ray detector controller 32 may be coupled to the x-ray detector 16 and to the main controller 30. The x-ray detector controller 32 may be configured to send an x-ray count rate to the main controller 30. A light source controller 52 may be coupled to the light source 50 and to the main controller 30. By way of the light source controller 52, the operation of the light source 50 may be controlled by the main controller 30.

A bias voltage controller 62 may be configured to apply and control a voltage bias between the specimen stage 24 and a conductor. By way of the bias voltage controller 62, the voltage bias between the specimen stage 24 and the conductor may be controlled by the main controller 30. The voltage bias generates an electric field between the conductor and the specimen. In one embodiment, the conductor may be a conductive grid 60 or conductive mesh. In another embodiment, the conductor may be a solid electrode conductor in the form, for example, of a ring, plate, or similar shape. In another embodiment, the conductor may be the vacuum changer of the system.

The apparatus may also include a current detector for detecting electrical current flowing between the sample and the stage apparatus generated by impingement of the charged-particle beam onto the area. The detected electrical current may be direct current (DC) or may be alternating current (AC). The detected electrical current may comprise a displacement current associated with capacitative charging.

Figure 2:
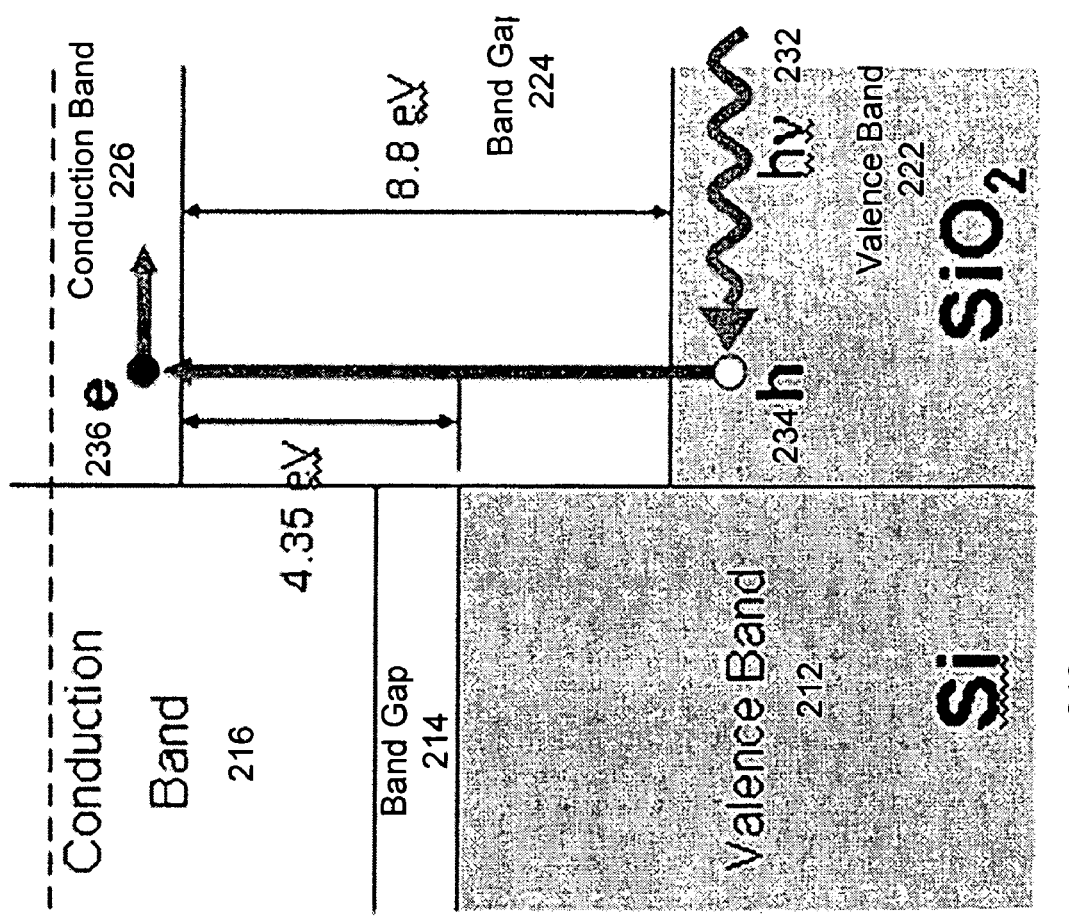
FIG. 2 is an energy band diagram of a sample in accordance with an embodiment of the invention.

FIG. 2 is an energy band diagram of a sample in accordance with an embodiment of the invention. The left side of the diagram represents the energy bands 210 of a silicon wafer substrate, and the right side of the diagram represents the energy bands 220 of a silicon dioxide surface layer. The silicon is a semiconductor material, and the silicon dioxide is an insulator. As depicted, in the silicon substrate, there is a valence band 212, a conduction band 216, and a band gap 214 therebetween. Similarly, in the silicon dioxide layer, there is a valence band 222, a conduction band 226, and a larger band gap 224 therebetween, the larger band gap 224 being due to the insulating nature of the silicon dioxide. When light with sufficiently short wavelengths is irradiated onto the wafer from the light source 50, then photons 232 of sufficiently high energy may create electronic carriers in the insulating material. The electronic carriers are created due to an electron from the valence band 222 absorbing the energy of the photon 232, becoming a conduction electron 236 and leaving behind a hole 234 in the valence band. The threshold for such a sufficiently high photon energy is determined by the band gap 224 in the insulating layer 220. When a substantial number of electronic carriers are created in the insulating layer 220, the layer 220 becomes electrically conductive.

In the particular embodiment shown in FIG. 2, that band gap 224 is approximately 8.8 electron volts (eV) for silicon dioxide, so that a light source with a wavelength of 141 nanometers (nm) or less would be effective. That wavelength range falls within the so-called vacuum ultraviolet (VUV) range of radiation. An example of such a source is a Deuterium lamp, such as the model L8998 available from Hamamatsu Corp. of Japan, which produces light substantially down to 121 nm wavelengths. Other sources of appropriate wavelength radiation could be used equally well, such as, but not limited to, lasers, plasma discharge systems, and longer wavelength sources used in conjunction with frequency multiplying materials. In other embodiments, the insulating (or semiconducting) material may be different, but the same principle may be applied, such that the material may be made conductive by way of irradiation with photons of sufficiently high energy.

Figure 3:
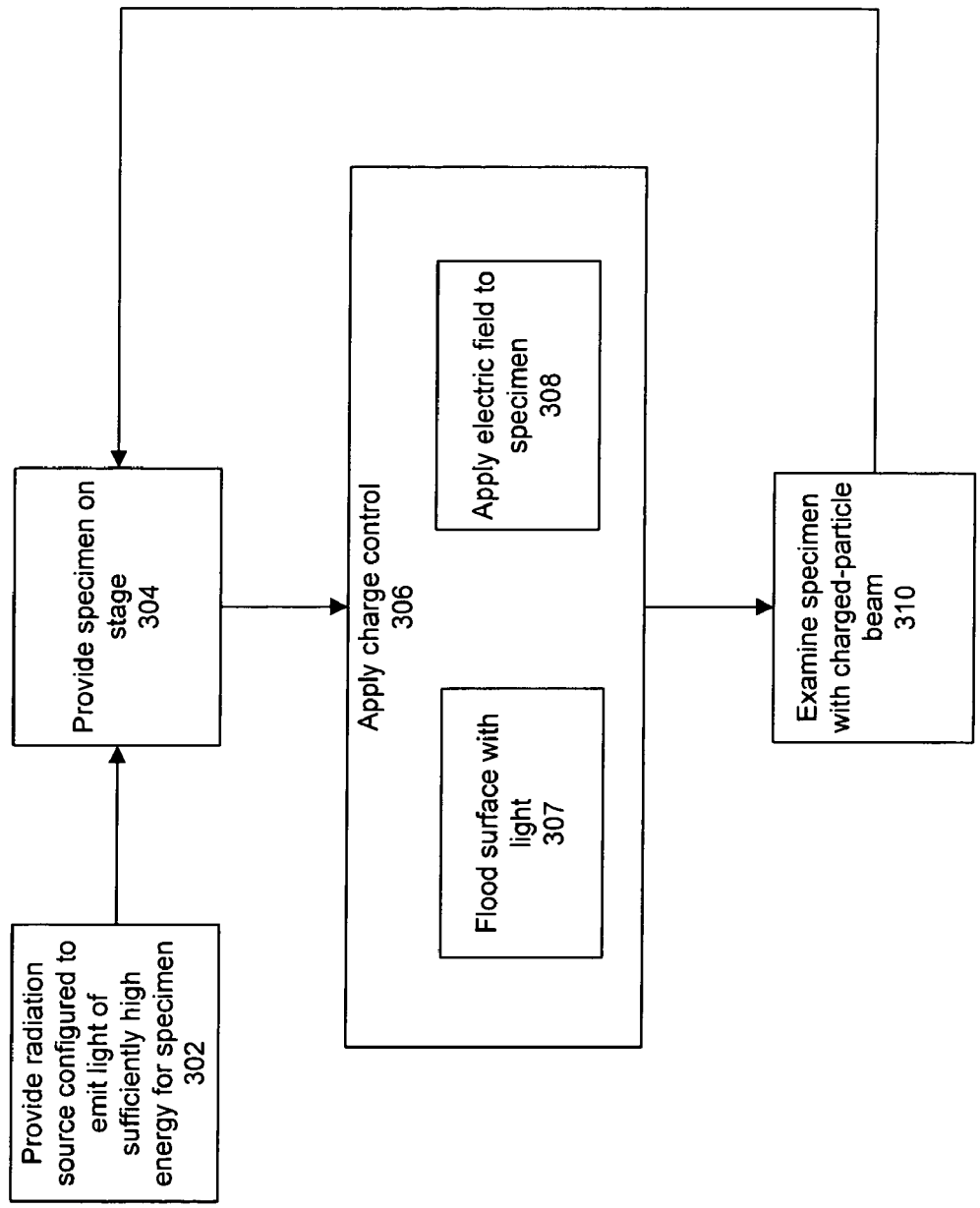
FIG. 3 is a flow chart of a method for sample charging control in accordance with an embodiment of the invention.

FIG. 3 is a flow chart of a method 300 for sample charging control in accordance with an embodiment of the invention. The light or radiation source 50 is provided (302). As discussed in relation to FIG. 2, the light source 50 is configured to emit light of sufficiently high energy compared to a band gap in the particular insulating specimen. In other words, the wavelength of the light must be short enough so as to be able to generate electronic carriers in the insulating specimen. In addition, a specimen or sample is provided (304) via the specimen stage 24.

Charge control is applied 306 by flooding (307) the surface of the specimen 20 with the light while at the same time applying (308) an electric field by means of a voltage bias to the specimen 20 or other means. The light may be flooded (307) onto the surface using the light source 50, and the bias voltage applied (308) between the stage 24 and the grid 60 using the bias voltage controller 62.

When the light is used to irradiate (307) the sample 20, charges embedded in the insulator (for example, trapped at the interface, or located on the exposed surface of the insulator) can move around within the insulator. Furthermore, additional charge can flow to and from the (semiconducting or conducting) substrate, and electrons may be emitted from the surface under the action of the photoelectric effect.

The controlled application (308) of the bias voltage results in the creation of an electric field between the sample 20 and the grid 60. Applicants have discovered that this advantageously controls the redistribution of charge during the irradiation (307). Another advantage is that, compared with an electron flood gun, it is easier to implement the light source 50 so as to provide the irradiation close to or coincident with the point of incidence of the primary beam 8 on the sample.

Thereafter, the specimen 20 may be examined (310) using the charged-particle beam. The examination may involve, for example, detecting electrons to form an image of the specimen 20, or detecting and analyzing x-rays stimulated by the beam 8 from the specimen 20. Subsequently, after the examination (310), the process 300 may loop back and another specimen may be provided (304) via the stage 24.

While the particular embodiment illustrated in FIG. 3 shows charge control being applied (306) prior to examination (310) for a specimen, the charge control (306) may be applied during the examination (310) or after the examination (310) in other embodiments.

Figure 4:
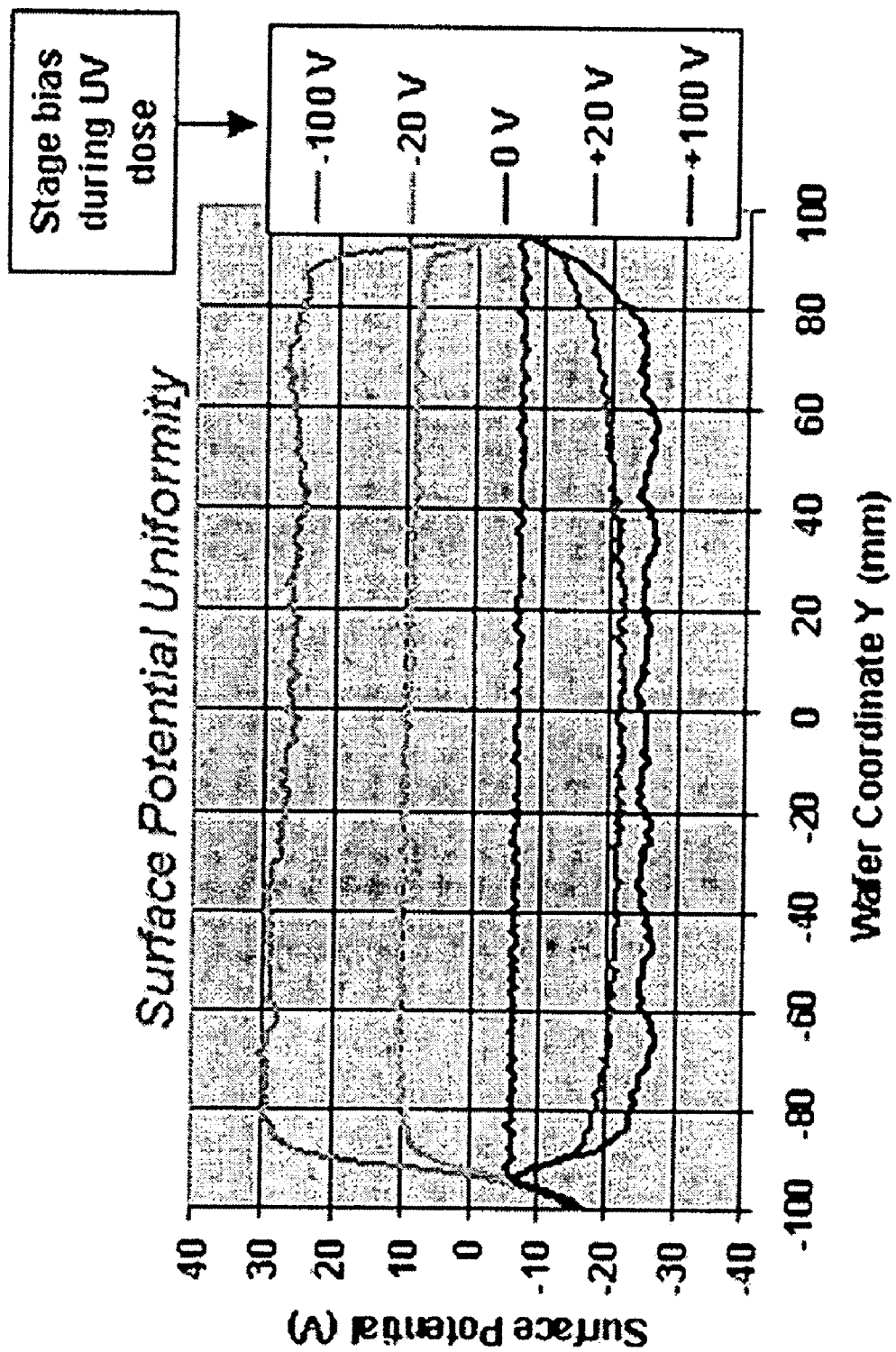
FIG. 4 is a graphic diagram showing the surface potential obtained by measurement for a sample wafer which was held at various stage bias voltages during UV dosage in accordance with an embodiment of the invention.

FIG. 4 is a graphic diagram showing the surface potential obtained by measurement for a sample which was held at various stage bias voltages during UV dosage in accordance with an embodiment of the invention. The sample comprised a silicon wafer with an insulating silicon dioxide layer thereon. Here, the apparatus comprised an electron beam imaging (EBI) instrument (similar to, but different than the ESX instrument shown in FIG. 1), and the irradiation in this instance was UV radiation from a VUV source. The surface potential was measured using a Kelvin probe.

In FIG. 4, the vertical axis represents the measured surface potential (in volts) and the horizontal axis represents the lateral position coordinate for the sample (in millimeters). Each curve in the Figure represents the surface potential measured after applying a particular stage bias voltage during the irradiation. The applied stage bias voltages (−100 V, −20 V, 0 V, +20 V, and +100 V) effectively resulted in corresponding applied electric fields.

As shown in FIG. 4, the method of applying the electric field in conjunction with the irradiation of sufficiently short wavelength light resulted in substantially flat or uniform surface potentials. Applicants believe this favorable result is due to the advantageous redistribution of charge in the sample. Furthermore, it is shown in FIG. 4 that the potential voltage level of the surface is controllable by varying the stage bias during the UV irradiation.

Figure 5:
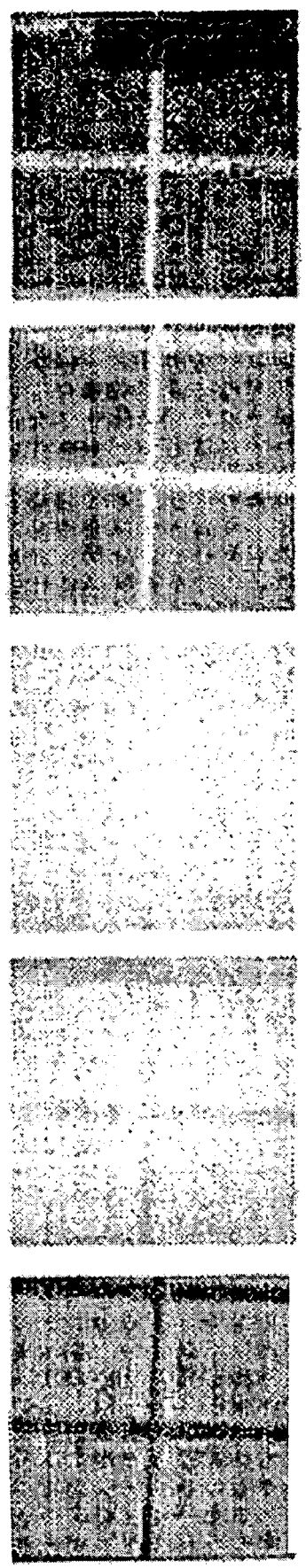
FIG. 5 is a series of electron images of a sample that was held at various stage bias voltages during UV dosage in accordance with an embodiment of the invention.

FIG. 5 is a series of electron images of a sample that was held at various stage bias voltages during UV dosage in accordance with an embodiment of the invention. Here, again, the sample comprised a silicon wafer with an insulating silicon dioxide layer thereon, the apparatus comprised an EBI instrument, and the irradiation in this instance is UV radiation from a VUV source. After the application of charging control, the images were obtained from scattered electrons generated due to impingement of the primary electron beam onto the wafer.

Images are shown in FIG. 5 as obtained after charging control using UV light and various applied sample bias voltages (−100 V, −10V, 0 V, +10 V, and +100 V). As shown, the images demonstrate that the method described provides a means for controlling the contrast of the sample. The images after charging control with applied bias voltages of −100 V and +100 V show more contrast than the images with applied bias voltages of −10 V and +10 V, while the image after charging control with no applied bias voltage (0 V) shows the least contrast. Furthermore, the contrast observed is shown to invert (light to dark and dark to light) when the polarity of the applied bias voltage is inverted.

The images in FIG. 5 indicate that the use of irradiation (of sufficiently short wavelengths) and applied specimen bias voltage together can advantageously improve images obtained in charged-particle beam systems. Although the images are obtained using an EBI instrument, similar results are expected with other systems, such as ESX systems, FIB systems, Auger spectroscopy systems, charged-particle beam reticle inspection systems, and other systems. Samples under test which could benefit from the use of such a method could include any sample which contains normally insulating or semiconducting materials, and are not limited to such samples commonly tested in the above noted systems.

The above-described diagrams are not necessarily to scale and are intended be illustrative and not limiting to a particular implementation. The above-described invention may be used in an automatic inspection or review system and applied to the inspection or review of wafers, optical masks, X-ray masks, electron-beam-proximity masks and stencil masks and similar substrates in a production environment.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A charged-particle beam apparatus configured for sample charging control prior to imaging a sample, the apparatus comprising:
    a stage configured to hold the sample;
    a column for generating a charged-particle beam and for directing the beam to an area of the sample;
    an electron detector for detecting electrons generated by impingement of the charged-particle beam onto the area;
    an irradiation source for generating a light beam and for directing the light beam to the area;
    a conductive element configured above the sample;
    bias circuitry configured to apply to the sample stage, during a charge control phase, a positive bias voltage relative to the conductive element above the sample; and
    control circuitry is coupled to the bias circuitry and to the irradiation source,
    wherein the control circuitry is configured to direct the light beam onto the area at a same time as said positive bias voltage is applied to the sample stage such that a substantially uniform negative surface potential is achieved.

2. The apparatus of claim 1, wherein the light beam comprises photons with energies higher than a band gap of the sample.

3. The apparatus of claim 2, wherein the sample comprises a surface insulating layer, and wherein the photons have energies higher than a band gap between valence and conduction bands of the insulating layer.

4. The apparatus of claim 1, wherein said bias voltage applied to the sample stage is varied during the charge control phase so as to enhance the contrast in subsequently obtained images.

5. The apparatus of claim 4, wherein the conductive element comprises a mesh configured above the sample.

6. The apparatus of claim 4, wherein the conductive element comprises a solid electrode.

7. The apparatus of claim 4, wherein the conductive element comprises a vacuum chamber of the apparatus.

8. The apparatus of claim 1, further comprising an x-ray detector for detecting x-rays generated by impingement of the charged-particle beam onto the area.

9. The apparatus of claim 8, wherein the charged-particle beam comprises an electron beam, and wherein the apparatus comprises an electron stimulated x-ray (ESX) instrument.

10. The apparatus of claim 1, further comprising a current detector for detecting electrical current flowing between the sample and the stage apparatus generated by impingement of the charged-particle beam onto the area.

11. The apparatus of claim 10, where the detected electrical current is direct current (DC).

12. The apparatus of claim 10, where the detected electrical current is alternating current (AC).

13. The apparatus of claim 10, where the detected electrical current is a displacement current associated with capacitive charging.

14. The apparatus of claim 4, wherein said bias voltage applied to the sample stage is variable over a range such that contrast is inverted in the subsequently obtained images.

15. The apparatus of claim 1, wherein the charged-particle beam comprises an electron beam, and wherein the apparatus comprises an electron beam imaging (EBI) instrument.

16. The apparatus of claim 1, wherein the charged-particle beam comprises an electron beam, and wherein the apparatus comprises an electron beam instrument for parametric measurement.

17. The apparatus of claim 1, wherein the control circuitry is configured to obtain x-ray data from the area using the charged-particle beam after the sample charging control is performed using the light beam.

18. The apparatus of claim 1, wherein the control circuitry is configured to obtain image data from the area using the charged-particle beam after the sample charging control is performed using the light beam.

19. The apparatus of claim 1, wherein the control circuitry is configured to obtain parametric data relating to the sample from the area using the charged-particle beam after the sample charging control is performed using the light beam.

20. A method of sample charging control in a charged-particle beam system configured to image a sample, the method comprising:
generating a light beam and irradiating the light beam onto an area of the sample held by a stage;
applying, concurrently with the irradiation by the light beam, a positive bias voltage to the stage relative to a conductive element configured above the sample such that a substantially uniform negative surface potential is achieved on the sample; and
subsequent to said concurrent irradiation and positive bias voltage application, generating a charged-particle beam and directing the charged-particle beam to the area so as to collect data from the area.

21. The method of claim 20, wherein the negative surface potential achieved is at least as negative as negative twenty volts.

22. The method of claim 20, wherein said positive bias voltage is at least positive ten volts.

23. The method of claim 20, wherein the sample charging control is also applied after the data collection to mitigate effects from the charged-particle beam.

24. A method of sample charging control in a charged-particle beam system configured to image a sample, the method comprising:
generating a light beam and irradiating the light beam onto an area of the sample held by a stage;
applying, concurrently with the irradiation by the light beam, a positive bias voltage to the stage relative to a conductive element configured above the sample such that a substantially uniform negative surface potential is achieved on the sample; and
at a same time as said concurrent irradiation and positive bias voltage application, generating a charged-particle beam and directing the charged-particle beam to the area so as to collect data from the area.

25. The method of claim 24, wherein the light beam comprises photons with energies higher than a band gap of the sample.

26. The method of claim 25, wherein the sample comprises a surface insulating layer, and wherein the photons have energies higher than a band gap between valence and conduction bands of the insulating layer.

27. The method of claim 24, wherein the said bias voltage is varied so as to enhance the contrast in the image.

28. The method of claim 27, wherein said bias voltage is variable over a range such that contrast is inverted in the image.

29. The method of claim 24, wherein the conductive element is comprised of the vacuum chamber.

30. The method of claim 24, wherein the charged-particle beam comprises an electron beam, and wherein the system comprises an electron stimulated x-ray (ESX) instrument.

31. The method of claim 24, wherein the charged-particle beam comprises an electron beam, and wherein the system comprises an electron beam imaging (EBI) instrument.

32. The method of claim 24, wherein the charged-particle beam comprises an electron beam, and wherein the system comprises a parametric measurement instrument.

33. A system of specimen charging control in a charged-particle beam apparatus configured for imaging a specimen, the system comprising:
means for irradiating a photon beam onto an area of the specimen held by a stage;
a conductive element configured above the specimen;
means for applying, concurrently with the irradiation by the photon beam, a positive bias voltage to the stage relative to the conductive element configured above the specimen such that a substantially uniform surface potential over a linear range of at least twenty millimeters is achieved on the specimen;
means for directing a charged-particle beam to the area so as to collect data from the area; and
an electron detector for detecting electrons generated by impingement of the charged-particle beam onto the area.

* * * * *